United States Patent [19]

Shelley

[11] Patent Number: 5,491,229
[45] Date of Patent: Feb. 13, 1996

[54] RAPAMYCIN DERIVATIVE

[75] Inventor: Peter R. Shelley, Dorking, England

[73] Assignee: SmithKline Beecham PLC, Brentford, England

[21] Appl. No.: 244,510

[22] PCT Filed: Dec. 1, 1992

[86] PCT No.: PCT/GB92/02235

§ 371 Date: Jun. 1, 1994

§ 102(e) Date: Jun. 1, 1994

[87] PCT Pub. No.: WO93/11130

PCT Pub. Date: Jun. 10, 1993

[30] Foreign Application Priority Data

Dec. 3, 1991 [GB] United Kingdom ............ 9125660

[51] Int. Cl.⁶ .................. A61K 31/305; C07D 491/00
[52] U.S. Cl. .................. 540/456; 435/119; 435/252.35
[58] Field of Search ............... 540/456; 514/291

[56] References Cited

U.S. PATENT DOCUMENTS 5,102,876  4/1992  Caufield ........................ 540/456

FOREIGN PATENT DOCUMENTS 0401747  12/1990  European Pat. Off. ............ 540/456
9102736   3/1991  WIPO ............................ 540/456
9113889   9/1991  WIPO ............................ 540/456

*Primary Examiner*—Robert T. Bond
*Attorney, Agent, or Firm*—Dara L. Dinner; Stephen Venetianer; Edward T. Lentz

[57] ABSTRACT

A compound of formula (I).

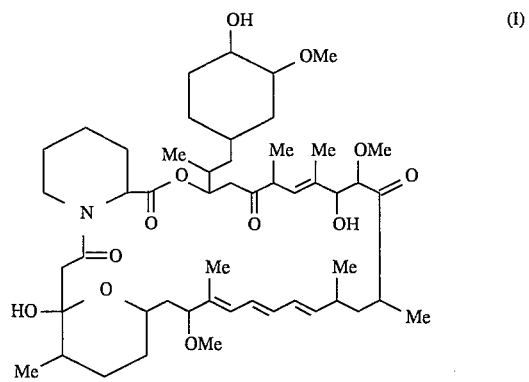

3 Claims, No Drawings

RAPAMYCIN DERIVATIVE

This application is a 371 of PCT/GB92/02235, filed Dec. 1, 1992.

The present invention relates to a novel compound and derivatives thereof, to processes for their production, to pharmaceutical formulations containing them, to their use in medical therapy, particularly in the treatment of bacterial and fungal infections, and also to their use as immunosuppressants and in treating carcinogenic tumours. Rapamycin is a known compound and is a member of the triene class of antibiotics. It was first isolated as an extract of the bacterium *Streptomyces hygroscopicus* and reported to have antifungal activity (British Patent 1436447). Subsequently rapamycin has been implicated as an immunosuppressant (Martel R. R. et al Can. J. Physiol. Pharmacol. 55, 48–51, 1977). At least one rapamycin-producing strain of *Streptomyces hygroscopicus* was deposited with the Northern Utilization and Research Division, Agricultural Research Service, U.S. Department of Agriculture, Peoria, Ill., U.S.A under accession number NRRL 5491. Rapamycin, and methods for its preparation by culturing NRRL 5491 are disclosed by U.S. Pat. No. 3,929,992 issued Dec. 30, 1975, the entire disclosure of which is hereby incorporated by reference.

A large number of microorganisms have been found to produce a variety of metabolites which have subsequently been isolated and have been shown to possess useful therapeutic properties. One such compound is 14-methylene rapamycin. This is believed to be a novel compound and has been found to have useful antifungal activity, anticancer activity and also immunomodulatory properties.

Accordingly the present invention provides a compound of the formula (I) which is believed to have the following structure:

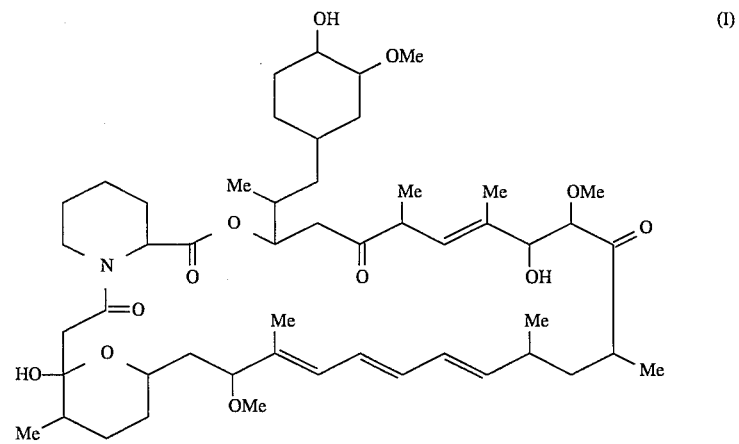

This novel compound has been found to have useful antimicrobial anticancer and immunomodulatory activity.

This compound is referred to as 14-methylene rapamycin according to the numbering system of J. Findlay et al., Can. J. Chem. (1980) 58, 579, however according to the more recent numbering system of J. McAlpine et al., J. Antibiotics (1991) 44, 688 this would be known as 9-methylene rapamycin.

The effect of the differing nomenclatures on the numbering of formula I is shown in formulas II and III below. Formula II represents 14-methylene rapamycin in one of its isomeric forms and formula III 9-methylene rapamycin.

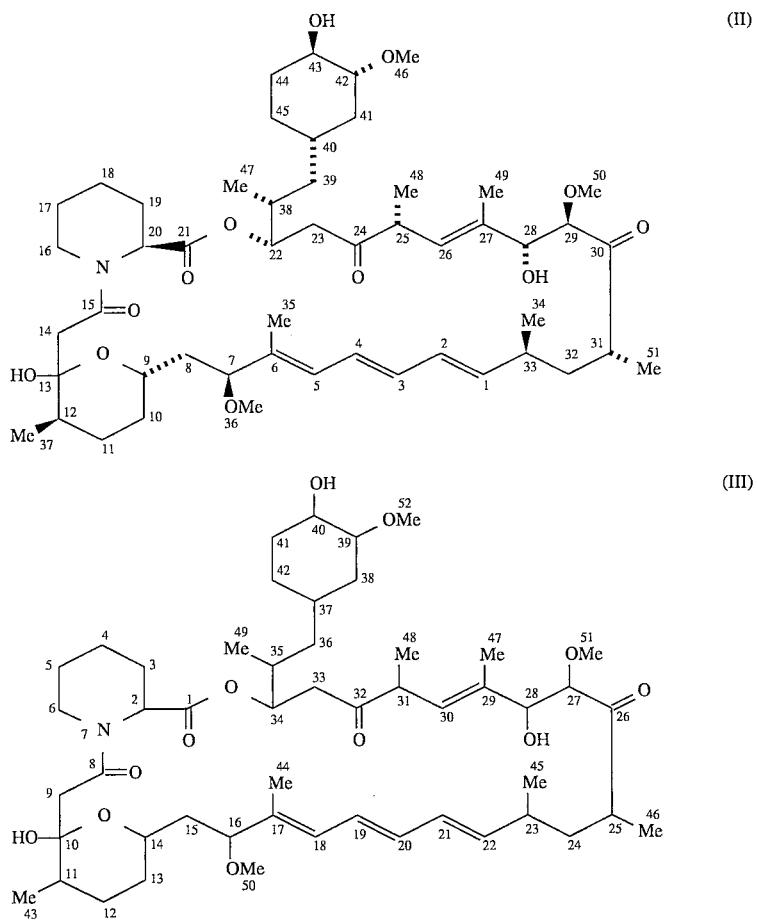

(II)

(III)

The compound could alternatively be referred to as 14-desoxorapamycin.

For simplicity, 14-methylene rapamycin is referred to in the following text, however where relevant both systems are also referred to.

The invention in a second aspect, further provides a process for the production of 14-methylene rapamycin which comprises cultivating a producing microorganism and subsequently isolating 14-methylene rapamycin or derivatives thereof.

The compound of the present invention has the following characteristics:

i) it has an apparent molecular weight of 899 by Fast Atom Bombardment (FAB) Mass spectroscopy, ii) it may be obtained by the cultivation of a microorganism from the genus Streptomyces, iii) $^{13}C$ NMR spectroscopy reveals 51 carbons in the molecule, iv) it has a characteristic UV spectrum with peaks at 268, 277 and 289 nm, v) it is useful as an antifungal agent, vi) it is useful as an immunomodulatory agent.

The compound of the present invention may be obtained by the cultivation of a producing organism and the recovery of it or a derivative thereof from the culture.

The term 'cultivation' (and derivatives of that term) as used herein means the deliberate aerobic growth of an organism in the presence of assimilable sources of carbon, nitrogen, sulphur and mineral salts. Such aerobic growth may take place in a solid or semi-solid nutritive medium, or in a liquid medium in which the nutrients are dissolved or suspended. The cultivation may take place on an aerobic surface or by submerged culture. The nutritive medium may be composed of complex nutrients or may be chemically defined.

It has been found that suitable microorganisms for use in the cultivation process according to the invention include bacterial strains belonging to the genus Streptomyces which are capable of elaborating 14-methylene rapamycin. It has further been found that an example of such a strain is sp. NCIB 40319 and also mutants thereof, which has been isolated from nature.

The term 'mutant' as used herein includes any mutant strain which arises spontaneously or through the effect of an external agent whether that agent is applied deliberately or otherwise. Suitable methods of producing mutant strains including those outlined by H. I. Adler in 'Techniques for the Development of Microorganisms' in 'Radiation and Radioisotopes for Industrial Microorganisms', Proceedings of a Symposium, Vienna, 1973, page 241, International Atomic Energy Authority, and these include:

(i) Ionizing radiation (e.g. X-rays and gamma-rays), u.v. light, u.v. light plus a photosensitizing agent (e.g. 8-methoxypsoralen), nitrous acid, hydroxylamine, pyrimidine base analogues (e.g. 5-bromouracil), acridines, alkylating agents (e.g. mustard gas, ethylmethane sulphonate), hydrogen peroxide, phenols, formaldehyde, heat, and (ii) Genetic techniques, including, for example, recombination, transformation, transduction, lysogenisation, lysogenic conversion, protoplast fusion and selective techniques for spontaneous mutants.

Using the methods of Becker B. Lechevalier M. P., Gordon R. E., Lechevalier H. A., 1964, Appl. Microbiol. 12, 421–423 and Williams S. T., Goodfellow M, Wellington E. M. H., Vickers J. C., Alderson. G., Sneath P. H. A., Sackin M. J., and Mortimer M. 1983 J. Gen. Microbiol. 129, 1815–1830, Sp. NCIB 40319 has been identified as a new, strain of *Streptomyces hygroscopicus* and therefore also forms a part of the present invention, particularly in biologically pure form. It has been deposited at the National Collection of Industrial and Marine Bacteria Ltd. (N.C.I.B), Aberdeen, Scotland under number 40319 on 14 Sep. 1990.

Strain NCIB 40319 has been characterised as follows:

The method of whole-cell amino acid analysis was that described by Becker et al (1964). Identification media used for the characterisation of the culture were as described by Williams et al (1983). In addition, starch casein agar (Waksman S. A., 1961. The Actinomycetes Vol. 2 Williams and Wilkins Co. Baltimore pp 1–363) was used for the morphological description of the culture.

The microorganism was characterised by inoculating agar blocks from a well grown plate into Y broth (see Table 1) and incubating for three days at 28° C. on a shaker. It was then centrifuged for 20 minutes at 3660 rpm, washed twice with distilled water, then finally resuspended in phosphate buffered saline (Dulbecco A). This inoculum was plated onto media commonly used for the identification of members of the Actinomycetales as above. Plates were incubated at 28° C. and the results were read at varying times but most were commonly taken at 14 days. The colours are described in common terminology but exact colours were determined by comparison with colour chips from the Methuen Handbook of colour (3rd Edn).

Results:

Cell Wall analysis

The whole-cell hydrolysates contained LL-diaminopimelic acid. The observations of growth and appearance of the organism were as follows:

Yeast extract-Malt extract Agar (ISP 2 Difco)

Growth good, cream 2 2a), with a white powdery centre. Colonies raised and rather wrinkled, no sporulation.

Inorganic Salts Starch Agar (ISP4 Difco)

Growth good, white with pale grey to grey (1 1b, 1 1c) aerial mycelium. Colonies quite flat with slightly raised centre. Reverse cream (2 2a).

Glycerol Asparagine Agar (S. A. Waksman, 1961, p328). medium No. 2.

Growth moderate to good, white with grey centre (1 1d). Colonies flat, reverse cream (2 2a).

Starch Mineral Salts Agar

Growth very poor, opaque small colonies. No aerial mycelium.

Starch Casein Agar

Growth good, white with light grey to grey central area (1 1c, 1 1d), occasional small patch of white non-sporulating mycelium in grey sporulating areas. Tiny colourless droplets over the grey areas. Colonies fairly flat and gently rounded. Small black hygroscopic patches may occur after 4 weeks incubation.

Morphological Properties

These were observed after two weeks incubation on starch casein agar: spore mass in grey colour-series; spore chains in section spirales, tightly coiled or slightly open, of small diameter, generally 2–6 coils, occasionally more, may aggregate into hygroscopic masses. There was no fragmentation of vegetative mycelium.

Biochemical Properties

See Table 2 for full details. In summary, melanin not produced; nitrate not reduced to nitrite in organic nitrate broth; $H_2S$ produced in peptone-yeast extract iron broth; no growth on inhibitors; degradation only of arbutin, antibiosis only against *Bacillus subtilis*. Carbohydrate utilization glucose, cellobiose, fructose, inositol, mannitol, raffinose, rhamnose and xylose. Nitrogen sources used: asparagine, histidine and hydroxyproline, α-amino-butyric acid used only slightly.

Determination of Identification Scores

These were obtained using the Matiden program (Sneath P. H. A., 1979. Computers and Geosciences 5 195–213) which provides the best identification scores for known or unknown strains against the percent probability matrix of Williams et al (1983). Willcox Probability—the nearer the score reaches 1.0, the better is the fit of an unknown with a group in the matrix (scores of >0.85 acceptable) Taxonomic distance—low scores indicate relatedness (scores <0.3 acceptable). The organism had acceptable identification scores with cluster 32 (violaceoniger) which contains *Streptomyces hygroscopicus* species.

Conclusion:

The culture is characterised by the grey spores in mass, the negative melanin reaction and the spores which are arranged in spirally coiled chains. The spore chains may coalesce into hygroscopic masses. The culture utilised a wide range of carbohydrate sources. The whole-cell hydrolysate indicates the presence of LL-diaminopimelic acid.

TABLE 1

| 1. Y broth | g/L |
|---|---|
| Special peptone (Oxoid) | 2.5 |
| Lab Lemco powder (Oxoid) | 2.5 |
| Tryptone (Oxoid) | 2.5 |
| Neutralized soya peptone (Oxoid) | 2.5 |
| Starch (BDH) | 2.5 |
| Glucose (BDH) | 2.5 |
| Malt Extract (Oxoid) | 2.5 |
| Glycerol (Fisons) | 2.5 |
| $CaCl_2.2H_2O$ (BDH) | 0.05 |
| $MgCl_2.6H_2O$ (Sigma) | 0.05 |
| NaCl (BDH) | 0.05 |
| $FeCl_3$ (Sigma) | 0.015 |
| $ZnCl_2$ (Sigma) | 0.0025 |
| $CuCl_2.2H_2O$ (Sigma) | 0.0025 |
| $MnSo_4.4H_2O$ (Sigma) | 0.0025 |
| $CoCl_2.6H_2O$ (BDH) | 0.025 |

TABLE 2

Biochemical Characteristics of NCIB 40319

| Test | Result |
|---|---|
| Melanin production | − |
| Use of Carbohydrates: | |
| Adonitol | − |
| Cellobiose | + |
| D-Fructose | + |
| Meso-Inositol | + |
| Inulin | − |
| Mannitol | + |
| Raffinose | + |
| L-Rhamnose | + Willcox Probability |
| D-Xylose | + |
| D-Glucose | + Cluster 32 violaceoniger = 0.936 |
| Use of Nitrogen sources: | |
| DL-α-Aminobutyric Acid | +/− |
| L-Histidine | + Taxonomic Difference |
| L-Hydroxyproline | + |
| Asparagine | + Cluster 32 violaceoniger = 0.284 |

TABLE 2-continued

Biochemical Characteristics of NCIB 40319

| Test | Result |
|---|---|
| Degradation of: | |
| Allantoin | − |
| Arbutin | + |
| Xanthine | − |
| Pectin | − |
| Lecithin | − |
| Nitrate Reduction | − |
| $H_2S$ Production | + |
| Growth on Inhibitors: | |
| Sodium azide (0.01% w/v) | − |
| NaCl (7.0% w/v) | − |
| Phenol (0.1% w/v) | − |
| Growth at 45° C. | − |
| Antibiosis to: | |
| *Aspergillus niger* | − |
| *Bacillus subtilis* | + |
| *Streptomyces murinus* | − |

The fermentation medium for cultivating sp. NCIB 40319 suitably contains sources of assimilable carbon and assimilable nitrogen together with inorganic salts. Suitable sources of nitrogen include yeast extract, soyabean flour, meat extract, cottonseed, flour, malt, distillers dried solubles, amino acids, protein hydrolysates and ammonium and nitrate nitrogen. Suitable carbon sources include glucose, lactose, maltose, starch and glycerol. Suitably the culture medium also includes alkali metal ions (for example, sodium), halogen ions (for example, chloride), and alkaline earth metal ions (for example calcium and magnesium), as well as trace elements such as iron and cobalt.

The cultivation may suitably be effected at a temperature of about 20° to 35° C., advantageously 20° to 30° C., and the culture may suitably be harvested up to 7 days, advantageously about 3 to 5 days, after the initiation of fermentation in order to give an optimum yield of the desired product.

The desired product or a derivative thereof may then be isolated from the culture medium and worked up and purified using conventional techniques for such compounds. All such isolation and purification procedures may conveniently be effected at cool to ambient temperature, for example at a temperature within the range of from 4° to 40° C., conveniently from 20° to 35° C.

The desired compound may readily be identified in a routine manner by testing for antifungal activity and/or by monitoring the h.p.l.c. retention time.

Suitably, the separation procedure may include a high-performance liquid chromatography step, preferably as the last step. Elution may be effected using aqueous methanol.

14-methylene rapamycin may be crystalline or non-crystalline and, if crystalline, may optionally be hydrated or solvated.

The compounds of the present invention can exist in free form or, where appropriate, in salt form. Pharmaceutically acceptable salts and preparation are well-known to those of skill in the art. The pharmaceutically acceptable salts of the compounds of this invention include the conventional non-toxic salts or the quaternary ammonium salts of such compounds which are formed, for example, from inorganic or organic acids of bases.

The compounds according to the invention are suitably provided in substantially pure form, for example at least 50% pure, suitably at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

14-methylene rapamycin has antifungal, anticancer and immunosuppressant properties and are useful for the treatment of fungal infections in animals, especially mammals, including humans, in particular humans and domesticated animals (including farm animals). Examples of pathogenic fungi include, but are not limited to *Candida albicans* and other candida species, *Microsporum gypsum, Trichophyton mentagophytes,* Aspergillus sp and Sporotrichum sp. The ability of the compound to inhibit the growth of pathogenic fungi may be demonstrated or predicted by standard tests known and used for this purpose, for example the yeast test described in the Examples. The compound may be used for the treatment of topical fungal infections in man caused by, among other organisms, species of Candida, Trichophyton, Microsporum or Epidermophyton or in mucosal infections caused by *Candida albicans* (e.g. thrush and vaginal candidiasis). It may also be used in the treatment of systemic fungal infections caused by, for example *Candida albicans, Cryptococcus neoformans, Aspergillus fumigatus,* Coccidiodes, Paracocciciodes, Histoplasma or Blastomyces spp. It may also be of use in treating eumycotic mycetoma, chromoblastomycosis and phycomycosis.

The compound of the invention is active as an immunomodulatory agent. The term "immunomodulatory agent" means that the compound of the invention is capable of inducing immune suppression by inhibiting T (and B) cell responses in vitro and/or by producing a statistically significant decrease in the inflammation system response mediated secondary lesion in the adjuvant induced arthritis. The fact that the compounds of this invention have utility in inducing immuno suppression means that they are useful in the treatment or prevention of resistance to or rejection of transplanted organs or tissues (eg kidney, heart, lung, bone marrow, skin, cornea, etc); the treatment or prevention of autoimmune, inflammatory, proliferative and hyperproliferative diseases, and of cutaneous manifestations of immunologically mediated diseases (eg rheumatoid arthritis, lupus erythematosus, systemic lupus erythematosus, Hashimotos thyroiditis, multiple sclerosis, myasthenia gravis, type 1 diabetes, uveitis, nephrotic syndrome, psoriasis, atopical dermatitis, contact dermatitis and further eczematous dermatitides, seborrheic dermatitis, Lichen planus, Pemplugus, bullous Phemphigold, Epidermolysis bullosa, uritcaris, angiodemas, vasculitides, erythemas, cutaneous eosinophilias, Alopecia areata, etc.); the treatment of reversible obstructive airways disease, intestinal inflammations and allergies (eg, Coeliac disease, proctitis, eosinophilia gastroenteritis, mastocytosis, Chrohn's disease and ulcerative colitis) and food related allergies (eg migraine, rhinitis, and eczema). Other indications for therapy using an immunomodulatory agent include, but are not limited to, the treatment of the following disease states: acute transplantation/graft rejection, progressive systemic sclerosis, multiple myeloma, atopic dermatitis, hyperimmunoglobulin E, hepatitis B antigen negative chronic active hepatitis, Familial Mediterranean fever, Grave's disease, autoimmune hemolytic anemia, primary biliary cirrhosis, inflammatory bowel disease and insulin dependent diabetes mellitus Accordingly the invention provides 14-methylene rapamycin or a derivative thereof for use in medical therapy.

Preferably for use as an antifungal agent or an anticancer agent or an immunomodulatory agent.

The invention further provides a method of treating a human or animal suffering from a fungal infection by the administration of an effective amount of 14-methylene rapamycin or derivative thereof.

Moreover, the invention provides a method of treating a human or animal in need of immunomodulation by administration of an effective amount of 14-methylene rapamycin or a derivative thereof.

The invention further provides a pharmaceutical composition comprising a compound of the formula (I) or a pharmaceutically acceptable salt thereof together with a pharmaceutically acceptable diluent or carrier. The composition is preferably for human use in tablet, capsule, injectable or cream form.

For human use, 14-methylene rapamycin or derivatives thereof can be administered alone, but will generally be administered in admixture with a pharmaceutical carrier selected with regard to the intended route of administration and standard pharmaceutical practice. For example, they may be administered orally in the form of a tablet containing such excipients as starch or lactose, or in a capsule or ovule either alone or in admixture with excipients, or in the form of an elixir or suspension containing a flavouring or colouring agent. They may be injected parenterally, for example, intravenously, intramuscularly or subcutaneously. For parenteral administration, they are best used in the form of a sterile solutions which may contain other substances, for example, enough salts or glucose to make the solution isotonic.

One skilled in the art would be able, by routine experimentation, to determine what an effective, non-toxic amount of compound would be for the purposes of inhibiting pathogenic fungi growth. Generally, however, an effective dosage will be in the range of about 0.05 to 100 milligrams per kilogram body weight per day.

For oral and parenteral administration to human patients suffering from a fungal infection, it is expected that the daily dosage level of the antifungal compounds of formula (I) will be from 0.1 to 10 mg/kg (in divided doses) when administered by either the oral or parenteral route. Thus tablets or capsules of the compounds can be expected to contain from 5 mg to 0.5 g of active compound for administration singly or two or more at a time as appropriate. The physician in any event will determine the actual dosage which will be most suitable for an individual patient and will vary with the age, weight and response of the particular patient. The above dosages are exemplary of the average case. There can, of course, be individual instances where higher or lower dosage ranges are merited, and such are within the scope of this invention.

One skilled in the art would be able, by routine experimentation, to determine what an effective, non-toxic amount of compound would be for the purpose of inducing immunosuppression. Generally, however, an effective dosage will be in the range of about 0.05 to 100 milligrams per kilogram body weight per day. For a human patient in need of immunomodulation the daily parenteral or oral dosage regimen for the compound or derivative thereof will preferably be from 0.1 mg/kg to 30 mg/kg.

The compounds of this invention should also be useful for treating carcinogenic tumors in a mammal. More specifically, the compounds should be useful for reducing tumor size, inhibiting tumor growth and/or prolonging the survival time of tumor-bearing animals. Accordingly, this invention also relates to a method of treating carcinogenic tumors in a human or other animal comprising administering to such human or animal an effective, non-toxic amount of a compound of Formula II. One skilled in the art would be able, by routine experimentation, to determine what an effective, non-toxic amount of compound would be for the purpose of treating carcinogenic tumors. Generally, however, an effective dosage is expected to be in the range of about 0.05 to 100 milligrams per kilogram body weight per day.

The compounds and compositions according to the invention may be formulated for administration in any convenient way for use in human or veterinary medicine, by analogy with other antifungal, anticancer or immunomodulatory agent.

The compounds and tablets and capsules for oral administration may be in unit dosage form, and may contain conventional excipients including, for example, binding agents, for example, syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerides), propylene glycol, or ethyl alcohol; preservatives, for example methyl or propyl p-hydroxybenzoate or sorbic acid; and, if desired, conventional flavouring and colour agents.

Compositions according to the invention intended for topical administration may, for example, be in the form of ointments, creams, lotions, eye ointments, eye drops, ear drops, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation. Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, propyleneglycol. The compound, depending on the vehicle and concentration used, may be either suspended or dissolved in the vehicle. Parenteral suspensions may be prepared in substantially the same manner except that the compound is suspended in the vehicle instead of being dissolved and sterilisation cannot be accomplished by filtration. The compound may instead be sterilised by exposure to ethylene oxide before being suspended in the sterile vehicle. Advantageously, a surfactant or wetting agent is included in such suspensions in order to facilitate uniform distribution of the compound.

It will be recognised by the person skilled in the art that the optimal quantity and spacing of individual dosages of the compound of the invention will be determined by the nature and extent of the condition being treated, the form, route and site of administration and the particular animal to be treated and that such optima can be determined by conventional techniques.

The following examples serve to illustrate the present invention.

EXAMPLE 1

Preparation of 14-methylene rapamycin from a culture of Streptomyces by fermentation A culture producing 14-methylene rapamycin has been classified as Streptomyces sp. and has been deposited in the national Collection of Industrial and Marine Bacteria, 23, St. Machar Drive, Aberdeen AB2 1RY, Scotland, UK. under the accession number NCIB 40319.

The culture was isolated from a termite hill at Abuke, Gambia.

1.0 Fermentation
1.1 Inoculum Preparation

Sporulating cultures grown on starch/casein agar slopes [soluble starch (BDH Poole, Dorset), 10 g/l; casein (white soluble), 1 g/l; $K_2HPO_4$, 0.5 g/l; $MgSO_4.7H_2O$, 0.5 g/l; agar technical (oxoid No.3, Oxoid Basingstoke) 18 g/l] in McCartney bottles were treated with 5 ml 0.02% Tween 80 to produce a spore suspension. Each of two 500 ml flasks containing 100 ml RS1 medium [Oxoid neutralised Soy peptone, 10 g/l; glucose monohydrate, 20 g/l; bakers yeast, 5 g/l; NaCl, 2 g/l; $ZnSO_4.7H_2O$, 0.05 g/l; $MgSO_4.7H_2O$, 0.125 g/l; $MnSO_4.4H_2O$, 0.01 g/l; $FeSO_4.7H_2O$, 0.02 g/l adjusted to pH 7.0 with 5N sodium hydroxide] were inoculated with 2 ml spore suspension. Flasks were incubated at 25° C., 240 rpm (50 mm throw) for 72 hours.

After 72 hours the contents of the 2 flasks were pooled and 16 ml aliquots of the pooled culture used to inoculate each of ten×2 liter flasks each containing 400 ml RS1 medium. Flasks were incubated at 25° C., 240rpm (50mm throw).

After 48 hours the contents were pooled and used to inoculate a further (tertiary) seed stage which comprised 100L RS1 medium+ 0.5 g/l NOPCO foamaster antifoam sterilised in situ in a 150 liter fermenter for 30 minutes at 121° C. The fermenter was run at 25° C., 180 rpm with an airflow of 50 l/min at 0.5 bar overpressure. Foaming was controlled by the addition of Pluriol PE8100 antifoam obtained from BASF, Cheshire; (20% solution in soya bean oil).

1.2 Final Stage Fermentation 3000 liters of RP2 medium [Arkasoy 50, 20 g/l obtained from Arkady Soy Mills, Manchester; glucose 20 g/l; L-lysine monohydrochloride, 6 g/l; bakers yeast, 6 g/l; NaCl, 5 g/l; $K_2HPO_4$, 2.5 g/l; $KH_2PO_4$, 2.5 g/l; $MgSO_4.7H_2O$, 0.125 g/l; $ZnSO_4.7H_2O$, 0.05 g/l; $MnSO_4.4H_2O$, 0.01 g/l; $FeSO_4.7H_2O$, 0.02 g/l; glycerol, 30 g/l; soya bean oil, 20 g/l] together with 0.5 g/l NOPCO Foamaster antifoam were sterilised in situ in a 4500 liter fermenter at 121° C. for 45 minutes. After sterilisation the pH was adjusted to pH 6.4 with 9M $NH_4OH$ and then inoculated with 100 liters of 56 hr tertiary seed culture.

The fermenter was run at 25° C., 67 rpm (0–11 h); 75rpm (11–84 h) and 90 rpm (84–202 h) with an airflow of 1500 l/min at 0.5 bar overpressure. Foaming was controlled by the addition of Pluriol PE8100 antifoam (20% solution in soya bean oil). The pH was allowed to fall naturally and no pH control was used. The fermenter was run for 158 h when 1000 liters of broth was removed from the vessel and the airflow was reduced to 1000 l/min to maintain a constant 0.5 vvm. The fermenter was run on for a further 44 h when the remaining 2100 liters of broth was harvested.

2.0 Isolation Procedure
2.1 Solvent Extraction

After 158 hr fermentation 1000 liters of whole broth were removed from the fermenter and adjusted to pH 4 with sulphuric acid. 500 liters of MIBK was added and the mixture stirred for 2 hours.

The solvent phase was recovered using a Westfalia SA7–03–076 liquid/solid centrifugal separator (Westfalia Separator Ltd; Oelde Germany). After concentration in vacuo to 20 L, the concentrate was stored at 5° C.

After 202 hrs fermentation the remaining 2100 liters of whole broth was removed from the fermenter and adjusted to pH 4 with sulphuric add. 1050 l of MIBK were added and the mixture stirred for 1 hour.

The solvent, phase was recovered as above and combined with the stored concentrate from above. The combined, rich MIBK extracts were concentrated to give a final volume of 68 L.

2.2 Solvent Partition

125 L of methanol and 125 L of hexane were added to the concentrate and the mixture stirred for ½ hour. Solvent phases were allowed to separate by gravity overnight. The upper phase was then recovered (190 L) and concentrated vacuo to give 7 kg of oil.

2.3 Initial Chromatographic Purification

The oil was loaded on a Diaion (Mitsubishi Chemical Industries Ltd Tokyo Japan) HP20 column (58×30 cm) packed in 10:90 acetone-$H_2O$.

After loading the column was eluted with 60:40 acetone-$H_2O$. Fractions were then taken and those containing rapamycin and 14-methylene rapamycin combined and then concentrated in vacuo to give an oil (500 g). The oil was dissolved in 2 liters of acetone and stored before silica chromatography.

2.4 Silica chromatography 2.5 L hexane was added to the stored acetone solution and the result loaded on a silica (Sorbsil C60 silica 40–60 μm, Rhone-Poulenc) column 33×30 cm packed in 85:15, hexane-acetone. Elution was with a step gradient of acetone in hexane. Fractions eluted with up to 70:30 hexane-acetone contained 14-methylene rapamycin, these were combined and concentrated in vacuo. 34 g of oil was obtained.

2.5 Amberchrom CG71 chromatography

2 L of Amberchrom CG71 50 μm–100 μm (Tosohaas, Stuttgart, Germany) were packed in a medium pressure liquid chromatograph (Jobin Yvon, France, 8 cm diameter) and equilibrated in hexane. After dissolving 34 g oil in toluene, elution continued at up to 8 bar pressure with 4 L of 80:20 hexane-ethyl acetate followed by 7.2 L 75:25 hexane-ethyl acetate. Fractions containing 14-methylene rapamycin were combined and evaporated in vacuo to give 1.0 g of solid.

2.6 Preparative hplc 800 mg of the above solid was dissolved in 76:24 methanol-$H_2O$ at up to 75 mg/ml and 2 ml portions injected separately onto a reverse phase 5 μm $C_{18}$ column and pre column (21.4 mm×25 cm and 21.4 mm×5 cm) (Rainin Instruments USA). After injection elution continued with 76:24 methanol-$H_2O$, at 15 ml/minute and was monitored for UV absorbance at 275 nm. Fractions containing the object compound from a total of six injections were pooled and concentrated in vacuo to yield 83 mg of white solid.

Fractions containing the object compound were analysed by reverse phase hplc using a Microsorb 5 μm $C_{18}$ column 4.6×250 mm (Rainin Instruments USA) and an Upchurch pre column (2.0×20 mm). This column was operated at 30° C. and monitored by ultraviolet absorbance at 275 nm. The column was eluted with methanol-water 74:26 at 1 ml/minute. Under these conditions the object compound designated 14-methylene rapamycin had a retention time of 31.4 minutes differing from that of rapamycin.

14-methylene rapamycin was characterised by ultra violet absorbance UV max 268,277,289 nm by mass spectroscopy FAB (M+Na)⁺=922 and by proton and $^{13}$C nuclear magnetic resonance spectroscopy.

3.0 Structural Analysis

Introduction

All NMR experiments were carried out on 18.5 mg/0.5 ml solution in $CDCL_3$/TMS. All measurements were carried out using a Bruker AM400 spectrometer at 300K. FAB MS data was recorded on a VG ZAB mass spectrometer using a matrix of 3-nitrobenzylalcohol and sodium acetate (NOBA/Na). Accurate mass measurements were carried out in duplicate using MNa⁺ ions from rapamycin and demethoxyrapamycin as reference ions.

Results

Molecular weight determinations after accurate mass measurements were 899.5739 and 899.5746. This is 14 mass units less than rapamycin (molecular formula $C_{51}H_{79}NO_{13}$) and is consistent with a formula of $C_{51}H_{81}NO_{12}$ and with the presence of a methylene in place of a carbonyl moiety in the parent rapamycin.

Evidence for the structure of 14-methylene rapamycin can be found in the results for $^1H$ and $^{13}C$ NMR spectra given in Table 3. In particular there is a loss of a carbonyl resonance in the $^{13}C$ NMR spectra and the addition of an isolated methylene in the $^1H$ and the $^{13}C$ NMR spectra. A COLOC experiment positively identified the $C_{14}/H_{14}$ isolated methylene system.

TABLE 3

A Table of $^1H$ and $^{13}C$ NMR Shifts (δ in ppm) for 14-Methylene (9-methylene)rapamycin

| 14-methylene rapamycin Atom No | 9-methylene rapamycin Atom No | δC | δH |
|---|---|---|---|
| 21 | 1 | 170.64 | — |
| 20 | 2 | 51.56 | 5.51 |
| 19 | 3 | 27.15 | 2.29, 1.77 |
| 18 | 4 | 20.66 | 1.78, 1.40 |
| 17 | 5 | 25.33 | 1.79, 1.55 |
| 16 | 6 | 43.52 | 3.90, 3.38 |
|  | 7 | — | — |
| 15 | 8 | 173.0 | — |
| 14 | 9 | 38.46 | 2.74, 2.43 |
| 13 | 10 | 97.98 | — |
| 12 | 11 | 39.11 | 1.45 |
| 11 | 12 | 27.51 | ~1.60 |
| 10 | 13 | 32.28 | ~1.65 |
| 9 | 14 | 65.81 | 3.58 |
| 8 | 15 | 38.53 | 1.70, 1.55 |
| 7 | 16 | 84.72 | 3.73 |
| 6 | 17 | 134.35 | — |
| 5 | 18 | 130.55 | 5.96 |
| 4 | 19 | 126.62 | 6.38 |
| 3 | 20 | 133.50 | 6.37 |
| 2 | 21 | 130.21 | 6.16 |
| 1 | 22 | 139.83 | 5.59 |
| 33 | 23 | 34.89 | 2.31 |
| 32 | 24 | 40.36 | 1.51, 1.18 |
| 31 | 25 | 41.24 | 2.86 |
| 30 | 26 | 217.20 | — |
| 29 | 27 | 85.41 | 3.60 |
| 28 | 28 | 77.76 | 4.14 |
| 27 | 29 | 136.69 | — |
| 26 | 30 | 127.18 | 5.40 |
| 25 | 31 | 46.80 | 3.40 |
| 24 | 32 | 208.78 | — |
| 23 | 33 | 41.08 | 2.72 |
| 22 | 34 | 75.96 | 5.13 |
| 38 | 35 | 33.12 | 1.98 |
| 39 | 36 | 38.72 | 1.16, 1.05 |
| 40 | 37 | 33.22 | 1.41 |
| 41 | 38 | 34.09 | 2.13, 0.68 |
| 42 | 39 | 84.42 | 2.95 |
| 43 | 40 | 73.90 | 3.38 |
| 44 | 41 | 31.24 | 1.99, 1.34 |
| 45 | 42 | 31.76 | 1.70, 1.02 |
| 37 | 43 | 16.94 | 0.89 |
| 35 | 44 | 9.81 | 1.61 |
| 34 | 45 | 21.48 | 1.03 |
| 51 | 46 | 13.76 | 1.01 |
| 49 | 47 | 12.43 | 1.75 |
| 48 | 48 | 16.07 | 1.13 |
| 47 | 49 | 16.21 | 0.94 |
| 36 | 50 | 55.64 | 3.13 |
| 50 | 51 | 59.94 | 3.35 |
| 46 | 52 | 56.52 | 3.41 |

EXAMPLE 3

COMPOSITION EXAMPLES A–H

A—CAPSULE COMPOSITION

A pharmaceutical composition of this invention in the form of a capsule is prepared by filling a standard two-piece hard gelatin capsule with 50 mg of a compound of the invention, in powdered form, 100 mg of lactose, 32 mg of talc and 8 mg of magnesium stearate.

B—INJECTABLE PARENTERAL COMPOSITION

A pharmaceutical composition of this invention in a form suitable for administration by injection is prepared by stirring 1.5% by weight of a compound of the invention in 10% by volume propylene glycol and water. The solution is sterilized by filtration.

C—OINTMENT COMPOSITION

Compound of the invention 1.0 g

White soft paraffin to 100.0 g

The compound of the invention is dispersed in a small volume of the vehicle and granually incorporated into the bulk of the vehicle of produce a smooth, homogeneous product. Collapsible metal tubes are then filled with the dispersion.

D—TOPICAL CREAM COMPOSITION

Compound of the invention 1.0 g

Polawax GP 200 20.0 g

Lanolin Anhydrous 2.0 g

White Beeswax 2.5 g

Methyl hydroxybenzoate 0.1 g

Distilled Water to 100.0 g

The polawax, beeswax and lanolin are heated together at 60° C. The compound of the invention is then added and dispersed throughout, and the composition is allowed to cool with slow speed stirring.

E—TOPICAL LOTION COMPOSITION

Compound of the invention 1.0 g

Sorbital Monolaurate 0.6 g

Polysorbate 20 0.6 g

Cetostearyl Alcohol 1.2 g
Glycerin 6.0 g
Methyl Hydroxybenzoate 0.2 g
Purified Water B.P. to 100.00 ml The methyl hydroxybenzoate and glycerin are dissolved in 70 ml of the water at 75. The sorbitan monolaurate, polysorbate 20 and cetostearyl alcohol are melted together at 75 C. and added to the aqueous solution. The resulting emultion is homogenized, allowed to cool with continuous stirring and the compound of the invention is added as a suspension in the remaining water. The whole suspension is stirred until homogenized.

F—EYE DROP COMPOSITION

Compound of the invention 0.5 g
Methyl Hydroxybenzoate 0.0 1 g
Propyl Hydrobenzoate 0.04 g
Purified water B.P. to 100.00 ml (B.P.=British Pharmacopia)

The methyl and propyl hydroxybenzoates are dissolved in 70 ml purified water at 75° C. and the resulting solution is allowed to cool. The compound of the invention is then added, and the solution is sterilized by filtration through a membrane filter (0.22 mum pore size) and packed aseptically into suitable sterile containers.

G—COMPOSITION FOR ADMINISTRATION BY INHALATION

For an aerosol container by a capacity of 15–20 ml: Mix 10 mg of a compound of the invention with 0.2–0.2% of a lubricating agent, such as polysorbate 85 or oleic acid, and disperse such mixture in a propellant, such as freon, preferably in a comination of (1,2 dichlorotetrafluoroethane) and difluorochloromethane and put into an appropriate aerosol container adapter for either intranasal or oral inhalation administration.

H—COMPOSITION FOR ADMINISTRATION BY INHALATION

For an aerosol container with a capacity of 15–20 ml: Dissolve 10 mg of a compound of the invention in ethanol (6–8 ml), add 0.1–0.2% of a lubricating agent, such as polysorbate 85 or oleic acid; and disperse such in a propellant, such as freon, preferably a combination of (1.2 dichlorotetrafluoroethane) and difluorochloromethane, and put into an appropriate aerosol container adapter for either intranasal or oral inhalation administration.

EXAMPLE 4

BIOLOGICAL EXAMPLES

The following assays were used.
Assay for Antifungal Activity

Yeast organisms (*Saccharomyces cerevisiae*) in logarithmic growth were plated on complete agar medium (YPD). The compound was dissolved in an appropriate aqueous or organic solvent and placed in wells punched in the agar. Plates were incubated for 48 hours and zones of inhibition were measured. The compound tested in this assay exhibited antifungal activity.

Mitogenesis Assay for Immunosuppressive Activity

Spleen cells from BDF1 female mice were established in RPMI with 10% fetal calf serum at $5 \times 10^6$/ml. One hundred ml aliquots of this suspension ($5 \times 10^5$ cells) were dispensed into 96-well round-bottomed microtiter plates (Linbro, Flow Laboratories). Concanavalin A (5 µg/ml) was added as the mitogenic stimulus, and the final volume in the microtiter wells was adjusted to 200 µL with RPMI. Cell cultures were incubated for 72 hours at 37 degrees C. in a 5% $CO_2$ atmosphere and pulsed with 0.5µ Ci $^3$H-thymidine (specific activity 2.00 Ci/mole) for the last 18 hour culture. The cells were harvested on an automated multiple sample harvester and cell-associated radioactivity counted in a Beckman liquid scintillation counter. The results are expressed as the mean values derived from quadruplicate measurements. Cell viability was determined by trypan blue exclusion after 72 hours of incubation. Compounds to be tested were added to the microtiter plates at the appropriate dilutions prior to the addition of cells. All of the compounds of the invention tested in this assay exhibited immunosuppressive activity.

Results of these two assays, i.e., antifungal activity assay and the mitogenesis assay for immunosuppressive activity, for compounds of this invention are provided in Table 3.

| Yeast $IC_{12}$ (nM) | Mitogenesis $IC_{50}$ (nM) |
|---|---|
| 13 | 15 |

$IC_{12}^{(nM)}$ refers to the concentration of drug in the antifungal assay which produces a 12 mm zone of inhibition. The aforementioned results in the antifungal and immunosuppression assay indicate that 14-methylene rapamycin has both antifungal and immunomodulatory activity.

While the above descriptions and Examples fully describe the invention and the preferred embodiments thereof, it is understood that the invention is not limited to the particular disclosed embodiments coming within the scope of the following claims.

I claim:
1. A compound of formula (I):

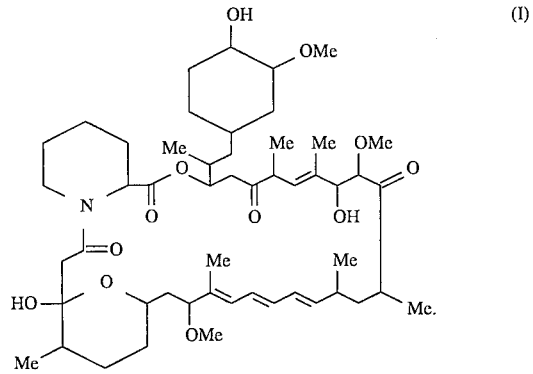

2. A compound characterised as follows:
    i) said compound has an apparent molecular weight of 899 by Fast Atom Bombardment (FAB) Mass spectroscopy;
    ii) said compound is obtainable by the cultivation of a microorganism from the genus Streptomyces;
    iii) said compound has 51 carbons in the molecule when subjected to $^{13}$C NMR spectroscopy;
    iv) said compound has a characteristic UV spectrum with peaks at 268, 277 and 289 nm.

3. A pharmaceutical composition comprising a pharmaceutically effective amount of the compound of claim 1 together with a pharmaceutically acceptable diluent or carrier.

* * * * *